United States Patent
Wang et al.

(10) Patent No.: US 8,481,790 B2
(45) Date of Patent: *Jul. 9, 2013

(54) CATALYST FOR PRODUCING UNSATURATED ALDEHYDE BY OXIDATION OF LOWER OLEFIN AT HIGH SPACE VELOCITY

(75) Inventors: Jian Wang, Shanghai (CN); Xuemei Li, Shanghai (CN); Yan Zhuang, Shanghai (CN); Kaimin Shi, Shanghai (CN); Kun Jiao, Shanghai (CN); Jianxue Ma, Shanghai (CN); Xiaodong Chu, Shanghai (CN); Jingming Shao, Shanghai (CN)

(73) Assignee: Shanghai Huayi Acrylic Acid Co., Ltd., Shanghai (CN)

( * ) Notice: Subject to any disclaimer, the term of this patent is extended or adjusted under 35 U.S.C. 154(b) by 58 days.

This patent is subject to a terminal disclaimer.

(21) Appl. No.: 13/116,309

(22) Filed: May 26, 2011

(65) Prior Publication Data

US 2011/0295041 A1    Dec. 1, 2011

(30) Foreign Application Priority Data

Jun. 1, 2010  (CN) .......................... 2010 1 0190267

(51) Int. Cl.
- *C07C 45/27* (2006.01)
- *B01J 27/192* (2006.01)
- *B01J 21/06* (2006.01)
- *B01J 23/00* (2006.01)

(52) U.S. Cl.
USPC ........... 568/471; 568/472; 502/212; 502/241; 502/242

(58) Field of Classification Search
USPC ..................... 568/471, 47; 502/212, 241, 242
See application file for complete search history.

(56) References Cited

U.S. PATENT DOCUMENTS

| 4,248,803 A | 2/1981 | Vanderspurt |
| 4,388,223 A | 6/1983 | Ferlazzo et al. |

FOREIGN PATENT DOCUMENTS

| CN | 11179206 | 7/1999 |
| CN | 101579631 | 11/2009 |

OTHER PUBLICATIONS

European Search Report dated Sep. 21, 2011, issued in related European Patent Application No. EP 11168441.

*Primary Examiner* — Sikarl Witherspoon
(74) *Attorney, Agent, or Firm* — Kilpatrick Townsend & Stockton LLP

(57) ABSTRACT

A method of preparing a catalyst for producing acrolein by oxidation of propylene at high space velocity, said catalyst is a Mo—Bi—Fe—Co based composite metal oxide. Producing unsaturated aldehyde via partial oxidation of lower unsaturated olefin at high space velocity using said catalyst is suitable for process with or without off-gas recirculating. Said catalyst is prepared by co-precipitation, the reaction conditions for using said catalyst to produce unsaturated aldehyde are, the space velocity of unsaturated lower olefin relative to catalyst being 120~200 h-1(STP), reaction temperature being 300~420° C. and absolute pressure being 0.1~0.5 MPa; a single-stage unsaturated lower olefin conversion ratio of greater than 98.0% and carbon oxide yield of less than 3.3% with an overall yield of unsaturated lower aldehyde and acid of greater than 94.0% are obtained. The process to prepare the said catalyst is simple, easy to be repeated, and capable of industrial scale-up.

9 Claims, No Drawings

CATALYST FOR PRODUCING UNSATURATED ALDEHYDE BY OXIDATION OF LOWER OLEFIN AT HIGH SPACE VELOCITY

This application claims benefit of Chinese patent application No. 201010190267.3, filed on Jun. 1, 2010, before the Chinese Intellectual Property Office, the disclosure of which is incorporated herein in its entirety by reference.

TECHNICAL FIELD

The present invention relates to a method for preparing a catalyst in chemical engineering field, particularly relates to a method for preparing a composite-metal-oxide based catalyst and a method for producing an unsaturated aldehyde via the partial oxidation of unsaturated lower olefin at high space velocity using the said catalyst, which catalyst can be used in a process with or without off-gas recirculating.

BACKGROUND ART

Unsaturated lower acids, including acrylic acids and methacrylic acids, are important organic chemical products. They are generally manufactured by a two-step oxidation of olefins, that is, partial oxidizing the olefins into aldehydes on an oxide catalyst containing molybdenum and bismuth, followed by further oxidizing the aldehyde products into corresponding acids on an oxide catalyst containing molybdenum and vanadium. Options such as increasing volume of the reactor or raising space velocity are applicable for enhancing the productivity of a manufacturing unit. Raising space velocity is certainly the most economic and convenient option.

There are a number of patents disclosing results on this field by various researchers.

JP-A-5-293389 discloses a catalyst represented by a formula of $Mo_aBi_bFe_cA_dX_eY_fZ_gSi_hO_i$, wherein Mo, Bi, Fe, Si, and O represent molybdenum, bismuth, iron, silicon and oxygen, respectively; A is at least one element selected from the group consisting of cobalt and nickel; X is at least one element selected from the group consisting of magnesium, zinc, manganese, calcium, chrome, niobium, silver, barium, tin, tantalum and lead; Y is at least one element selected from the group consisting of phosphorus, boron, sulfur, selenium, cerium, tungsten and titanium; Z is at least one element selected from the group consisting of lithium, sodium, potassium, rubidium, cesium and thallium; and each of a, b, c, d, e, f, g, h and i represents the atomic ratio of each element, with the proviso that when a=12, b=0.01 to 3, c=0.01 to 5, d=1 to 12, e=0 to 6, f=0 to 5, g=0.001 to 1, and h=0 to 20, and i is the oxygen atom number needed to satisfy the atomic valence of each element. When gas-phase catalytic oxidation of propylene is performed by using the above catalyst to produce acrolein and acrylic acid, the yield of acrylic acid is 6.2 mole % under a propylene conversion ratio of 99.1 mole % and an acrolein selectivity of 89.6 mole %, the space velocity of propylene against the catalyst is 60~90 hr$^{-1}$(STP) during the process.

In Chinese Patent application CN93103817.1, Lanzhou Petrochemical Research Institute discloses a catalyst represented by a formula of $MoBiFeWX^1X^2X^3X^4$, wherein $X^1$ is Co or Ni, $X^2$ is at least one element selected from alkali metal or alkaline earth metal, $X^3$ is at least one element selected from zinc, phosphorus, arsenic and boron, $X^4$ is at least one element selected from silicon, aluminum, and titanium, based on the numbers of Mo atom being 12, the amount of Bi is 0.5~4, Fe is 0~8, W is 0~4, $X^1$ is 1~8, $X^2$ is 0.05~3, $X^3$ is 0~4, and $X^4$ is 0~16. During the preparation of the catalyst, molybdenum oxide is used as a raw material to replace part of the ammonium molybdate raw material, and basic bismuth carbonate is used as a raw material to replace part of the bismuth nitrate raw material, and no pore-forming agent is necessary. The active ingredients are homogenously mixed with a silica micro-powder at a predetermined ratio, then silica gel is added thereinto and the mixture is band extruded, the extruded product is fired at 460° C. for 6 hours to produce the finished catalyst. Assessment on the catalyst is performed in a stainless steel pipe (Φ25.4 mm) packed with 1.0 L of the catalyst, a gas mixture with 10 wt % of propylene, 73 wt % of air and 17 wt % of steam is passed therethrough at a space velocity of 60 h$^{-1}$(STP), acrylic acid and acrolein are produced with a yield of 93.2% under a propylene conversion ratio of 98.5% at a reaction temperature of 315° C., while the yield of COx is 4.2%.

In Chinese Patent application CN 00804787.1, BASF AG discloses a sphere-shaped or hollow-cylinder-shaped catalyst represented by a formula of $Mo_{12}Bi_aFe_bX^1_cX^2_dX^3_eX^4_fO_x$, wherein $X^1$ is nickel and/or cobalt, $X^2$ is thallium, an alkali metal and/or an alkaline earth metal, $X^3$ is zinc, phosphorus, arsenic, boron, antimony, tin, cerium, lead and/or tungsten, $X^4$ is silicon, aluminum, titanium and/or zirconium. Based on the number of molybdenum atoms being 12, a is from 0.5 to 4, b is from 0.01 to 5, c is from 0 to 10, d is from 0 to 2, e is from 0 to 8, and f is from 0 to 10. Assessment on the catalyst is performed in a stainless steel pipe (Φ26 mm) adopting an off-gas recirculating process at a space velocity of propylene being 120 h$^{-1}$(STP), composition of the gaseous reactant comprises 6~6.5 wt % propylene, 10.4~10.7 wt % $O_2$, 0.3~0.5 wt % CO, 0.8~1.2 wt % $CO_2$, 0.025~0.04 wt % acrolein and 3~3.5 wt % steam, and balance of $N_2$. The reactor applies an innovative method for two-stage temperature control, acrylic acid and acrolein are produced with a yield of 92.7% under a propylene conversion ratio of 94.5% when the temperature for the first reaction stage is 325° C. and the temperature for the second reaction stage is 347° C.

In Chinese Patent application CN 01116867, Nippon Shokubai Co., Ltd. discloses a hollow-cylinder-shaped catalyst represented by a formula of $MoBiFeWX^1X^2X^3X^4X^5$, wherein $X^1$ is cobalt and/or nickel, $X^2$ is at least one element selected from alkali metal and thallium, $X^3$ is an alkaline earth metal element, $X^4$ is at least one element selected from zinc, phosphorus, arsenic, boron, thallium, antimony, tin, cerium, niobium, and manganese, $X^5$ is at least one element selected from silicon, aluminum, titanium, and zirconium, based on the numbers of Mo atom being 12, the number of Bi atom is 0.1~10, Fe is 0.1~20, W is 0~10, $X^1$ is 2~20, $X^2$ is 0.001~10, $X^3$ is 0~10, $X^4$ is 0~4, and $X^5$ is 0~30. Assessment on the catalyst is performed in a stainless steel pipe (Φ25 mm) at a space velocity of propylene being 115 h$^{-1}$(STP), composition of the gaseous reactant comprises 7 wt % propylene, 14 wt % $O_2$, 25 wt % steam, and balance amount of $N_2$. Acrylic acid and acrolein are produced with a yield of 94.2% under a propylene conversion ratio of 98.5% at a reaction temperature of 310° C.

In Chinese Patent application CN 95115847, Mitsubishi Chemical Corp. discloses a hollow-cylinder-shaped catalyst represented by a formula of $MoBiFeCoNiX^1X^2X^3$, wherein $X^1$ is an alkali metal and/or thallium atom, $X^2$ is at least one element selected from magnesium, calcium, zinc, cerium, samarium and halogen, $X^3$ is at least one element selected from tungsten, phosphorus, arsenic, and boron. Based on the numbers of Mo atom being 12, the numbers of Bi atom is 0.5~7, Fe is 0.05~3, Co+Ni is 1~10, $X^1$ is 0.04~2, $X^2$ is 0~2, $X^3$ is 0~3. Assessment on the catalyst is performed in a stainless steel pipe (Φ25 mm) at a space velocity of propylene of 90 h$^{-1}$(STP), composition of the gaseous reactant comprises 10 wt % propylene, 73 wt % air, and 17 wt % steam. Acrylic acid and acrolein are produced with a yield of 95.1% under a propylene conversion ratio of 98.5% at a reaction temperature of 315° C.

In Chinese patent application CN 200480004485, Nippon Kayaku Co., Ltd. discloses a coated spherical catalyst represented by a formula of MoBiFeCoNiX$^1$X$^2$, wherein X$^1$ is an alkali metal and/or thallium element, X$^2$ is at least one element selected from tin, zinc, tungsten, chromium, manganese, magnesium, antimony and titanium. Based on the numbers of Mo atom being 12, the numbers of Bi atom is 0.1~7, Fe is 0.5~8, Co+Ni is 0.5~20, X$^1$ is 0~1, X$^2$ is 0~2. Assessment on the catalyst is performed in a stainless steel pipe (Φ25 mm) at a space velocity of propylene being 90 h$^{-1}$ (STP), composition of the gaseous reactant comprises 8.3 wt % propylene, 14 wt % O$_2$, 24.8 wt % steam, and balance of N$_2$. Acrylic acid and acrolein are produced with a yield of 90.9% under a propylene conversion ratio of 98.1% at a reaction temperature of 330° C., while the yield of COx is 4.2%.

In most of aforementioned patents concerning catalysts for making aldehyde from unsaturated lower olefin, inventors adopt a process without off-gas recirculating with the highest space velocity of about 90 h$^{-1}$(STP) except the 115 h$^{-1}$(STP) in the patent of Nippon Shokubai, meanwhile, BASF AG utilizes a process with off-gas recirculating during propylene oxidation, wherein the volume space velocity of propylene relative to the catalyst can reach 120 h$^{-1}$(STP). Raising the space velocity of olefin will cause various problems, which is particularly notable in non-off-gas-recycling processes, the most obvious problems are diminished yield and lower activity of the catalyst, in addition, overhigh temperature of the hotspot due to heat accumulation induced by increased heat generation, higher yield of COx and lower selectivity are apparent as well.

DISCLOSURE OF THE INVENTION

In view of the aforementioned problems, this invention is directed to provide a method for preparing a Mo—Bi—Fe—Co based composite-metal-oxide catalyst, as well as a method for producing unsaturated aldehyde via the partial oxidation of unsaturated lower olefin at high space velocity using the said catalyst, which method is suitable for a process with or without off-gas recirculating. The said method for preparing the catalyst is characterized in that the precursor compounds for forming the catalyst are co-precipitated to obtain a slurry at pH 1.5~3.0, the slurry, within which a diluting thermal conductor is optionally added, is then dried in any apparatus capable of quick drying same, the dried product is then molded and fired to produce the finished catalyst. Said catalyst product is suitable for reactions of olefin at a volume space velocity relative to catalyst of 120 h$^{-1}$(STP) or higher to produce corresponding aldehyde at high activity and high yield. The problem of hotspot accumulation is effectively solved by mixing a diluting thermal conductor having excellent heat conductivity into the catalyst, therefore, the catalyst possesses high selectivity.

Therefore, the object of the present invention is to provide a method for preparing a Mo—Bi—Fe—Co based composite-metal-oxide catalyst and a method for producing unsaturated aldehyde via the partial oxidation of unsaturated lower olefin at high space velocity using the said catalyst in a process with or without off-gas recirculating.

As used herein, the term, lower olefin, refers to an ethylenically unsaturated olefin having from 3 to 6 carbon atoms, preferably from 3 to 5 carbon atoms, such as propylene, iso-butylene and the like.

As used herein, the term, unsaturated aldehyde, refers to that obtained by the oxidation of said lower olefin. Said unsaturated aldehyde can be, for example, acrolein, methacrolein and the like.

In one aspect of the invention, there is a method for preparing a catalyst for forming acrolein by oxidation of propylene at high space velocity, wherein said catalyst is a Mo—Bi—Fe—Co based composite metal oxide represented by a formula of $Mo_aBi_bFe_cCO_dX_eY_fZ_gO_h$, wherein Mo is a molybdenum atom; Bi is a bismuth atom; Fe is an iron atom; Co is a cobalt atom; X is at least one atom selected from tungsten (W), antimony (Sb), arsenic (As), phosphorus (P), nickel (Ni), tin (Sn), and plumbum (Pb); Y is at least one atom selected from zinc (Zn), chromium (Cr), manganese (Mn), ruthenium (Ru), silver (Ag), palladium (Pd) and ruthenium (Ru); and Z is at least one atom selected from sodium (Na), potassium (K), lithium (Li), rubidium (Rb), cesium (Cs), calcium (Ca), magnesium (Mg), strontium (Sr), and barium (Ba); and each of a, b, c, d, e, f and g represents the atomic ratio of each atom, with the proviso that when a=12, b=0.1~7, c=0.5~8, d+e=0.5~20, f=0~1, g=0~2, and h is a number determined by the oxidation state of each atom; said catalyst is obtained by co-precipitation, i.e. the precursor compounds for the catalyst are co-precipitated to obtain a slurry at pH 1.5~3.0, the slurry is rapidly dried, then a diluting thermal conductor is added and the mixture is molded and fired to produce the finished catalyst; alternatively, the diluting thermal conductor can be added into the slurry prior to the rapid drying, then the dried mixture is molded and fired to produce the finished catalyst.

In another aspect of the invention, there is a catalyst composition comprising 60-90% by weight of a catalyst and 10-40% by weight of a diluting thermal conductor, wherein said catalyst is a Mo—Bi—Fe—Co based composite metal oxide represented by a formula of $Mo_aBi_bFe_cCO_dX_eY_fZ_gO_h$, wherein Mo is a molybdenum atom; Bi is a bismuth atom; Fe is an iron atom; Co is a cobalt atom; X is at least one atom selected from tungsten (W), antimony (Sb), arsenic (As), phosphorus (P), nickel (Ni), tin (Sn), and plumbum (Pb); Y is at least one atom selected from zinc (Zn), chromium (Cr), manganese (Mn), ruthenium (Ru), silver (Ag), palladium (Pd) and ruthenium (Ru); and Z is at least one atom selected from sodium (Na), potassium (K), lithium (Li), rubidium (Rb), cesium (Cs), calcium (Ca), magnesium (Mg), strontium (Sr), and barium (Ba); and each of a, b, c, d, e, f and g represents the atomic ratio of each atom, with the proviso that when a=12, b=0.1~7, c=0.5~8, d+e=0.5~20, f=0~1, g=0~2, and h is a number determined by the oxidation state of each atom; characterized in that said catalyst is obtained by a process comprises the steps of: co-precipitating the precursor compounds for the catalyst, forming a slurry at pH 1.5~3.0; rapidly drying the slurry; adding a diluting thermal conductor and molding the mixture; and firing to produce the finished catalyst; alternatively, the diluting thermal conductor can be added into the slurry prior to the rapid drying, then the dried mixture is molded and fired to produce the finished catalyst.

In one embodiment, the catalyst composition comprising 70-80% by weight of a catalyst and 20-30% by weight of a diluting thermal conductor.

In the composite metal oxide of the catalyst, the molybdenum atom is derived from at least one of phosphomolybdic acid, molybdate and molybdenum oxide; the tungsten atom is derived from at least one of tungstate and tungsten trioxide;

the alkali metal or alkaline earth metal atom is derived from its corresponding hydroxide or nitrate; and other atoms are derived from their corresponding acetate, nitrate, chloride or oxide.

The said composite-metal-oxide catalyst is prepared by co-precipitation, i.e. the precursor compounds for the catalyst are co-precipitated by using basic solution to adjust the pH, until the pH of the slurry reaches 1.5~3.0, wherein the basic solution is selected from ammonia or aqueous solution of urea. The said slurry of precursor compounds or the slurry containing the diluting thermal conductor is then dried in any apparatus capable of drying the slurry into dried powder having water content of between 8 to 10 wt % within 1.8~2.2 hours. The obtained dried powder of precursor compounds is homogenously mixed with the diluting thermal conductor, a binder and a molding aids, or the obtained dried powder of the diluting thermal conductor-containing slurry is homogenously mixed with a binder and a molding aids, and the obtained mixture is coated onto an inert carrier or directly molded by compression or band extrusion to form solid or hollow particles in the shape of sphere, cylinder, trefoil, quatrefoil, or gear. The amount of the diluting thermal conductor is 0-50%, preferably 10-45%, more preferably 15-35% by weight of the total dried powder, the amount of the binder is 0.01-10% by weight of the total dried powder and the amount of the molding aids is 0.01-10% by weight of the total dried powder. The diluting thermal conductor described herein is a silicon powder. The molded catalyst is fired at a temperature of 420~550° C. for 1~20 hours in an atmosphere having oxygen amount of 1~21 wt % and comprising oxygen molecules as well as balance amount of nitrogen, steam, helium, argon, or any combination thereof, and during firing, the volume space velocity of the firing gas relative to the catalyst is in the range of 10~1500 h$^{-1}$, and the oxygen molecule is derived from air or pure oxygen gas.

The Mo—Bi—Fe—Co based composite-metal-oxide catalyst according to the present invention can be used in the reaction for producing acrolein by the partial oxidization of propylene or producing methacrolein by the partial oxidation of isobutylene or t-butyl alcohol, such reactions can be performed in a process with or without off-gas recirculating. The conditions of the reaction can be as follows, the volume space velocity of propylene or isobutylene relative to the catalyst is in the range of 120~150 h$^{-1}$(STP), the reaction temperature is in the range of 300~420° C., the absolute pressure is in the range of 0.1~0.5 MPa, the molar ratio of oxygen to propylene or isobutylene is in the range of 1~10, and the molar ratio of steam to propylene or isobutylene is in the range of 1~15.

In summary, a single-stage unsaturated lower olefin conversion ratio of greater than 98.0% and carbon oxides yield of less than 3.3% with an overall acrylic acid and acrolein yield of greater than 94.0% can be obtained by using the Mo—Bi—Fe—Co based composite metal oxide described in the present invention as a catalyst at a space velocity of the unsaturated lower olefin relative to the catalyst of 120~200 hr$^{-1}$(STP) and a reaction temperature of 300~400° C. and an absolute pressure of 0.1~0.5 MPa. The process to prepare the said catalyst is simple, easy to be repeated, and capable of being used in an industrial scale.

DESCRIPTION OF THE PREFERRED EMBODIMENT OF THE INVENTION

The following Examples are offered as further illustration of the invention and are not to be construed as limitations thereof. The conversion ratio of the raw unsaturated lower olefin and the selectivity of the unsaturated aldehyde in the examples are computed according to the following equations, $$\text{Conversion Ratio of Unsaturated Lower Olefin} = \frac{\text{Depleted Unsaturated Lower Olefin (mole)}}{\text{Input Unsaturated Lower Olefin (mole)}} \times 100\%$$

$$\text{Selectivity of Unsaturated aldehyde} = \frac{\text{Formed Unsaturated Aldehyde(mole)}}{\text{Depleted Unsaturated Lower Olefin (mole)}} \times 100\%$$

Example 1

First, 3000 ml water was added into a beaker and heated to 60° C., 1450.5 g ammonium molybdate and 6.3 g potassium nitrate were added thereto, the mixture was stirred to dissolve and form a solution (A), which was maintained at 70° C. Next, 1300 ml water was added into another beaker and warmed up to 50° C., 1109.0 g cobalt nitrate, 533.0 g nickel nitrate and 488.9 g ferric nitrate were added thereto sequentially, the mixture was stirred to dissolve, then 30 ml nitric acid and 570.4 g bismuth nitrate were added thereto, the mixture was stirred to dissolve and form a solution (B), which was maintained at 50~70° C. Solution (B) was added dropwise into solution (A) with intense stirring at 70° C., in the meantime ammonia was added to keep pH of the slurry at 2.5, and the mixture was stirred after the addition was finished until the slurry is homogenously mixed. The slurry was dried at 135° C. for 18 hours, followed by treated at 210° C. for 15 hours. The obtained powder was mixed with silicon at 7:3 ratio, and 3 wt % graphite and 2 wt % (based on silica) silica gel were added, the mixture was compression molded into a 3 mm long hollow cylinder with an external diameter of 5 mm and internal diameter of 2 mm, and fired at 510° C. to produce the finished catalyst.

50 g of the catalyst was filled into a stationary bed tubular reactor, preheated gas mixture of propylene, air, steam and nitrogen with a molar ratio of propylene:oxygen:water:nitrogen other than that from air being 1:1.8:1.5:2.5 was passed through the reactor at an overall space velocity of 1850 h$^{-1}$, the oxidation reaction was conducted at 320° C. under normal pressure. After 50 hours of reaction at 342° C., the propylene conversion ratio was 98.4%, acrolein yield was 82.0%, acrylic acid yield was 8.8%, and COx yield was 3.2%.

Example 2

The catalyst was prepared as described in Example 1 except that the drying process for the catalyst formulation was adjusted to dry at 155° C. for 18 hours followed by treating at 210° C. for 15 hours. The reaction conditions were also the same as those of Example 1. After 50 hours of reaction at 345° C., the propylene conversion ratio was 98.3%, acrolein yield was 84.3%, acrylic acid yield was 9.1%, and COx yield was 2.9%.

Example 3

The catalyst was prepared as described in Example 1 except that the drying process for the catalyst formulation was adjusted to spray dry at 180° C. followed by treating at 210° C. for 15 hours. The reaction conditions were also the same as those of Example 1. After 50 hours of reaction at 343° C., the propylene conversion ratio was 98.5%, acrolein yield was 84.9%, acrylic acid yield was 9.5%, and COx yield was 2.8%.

Example 4

The catalyst was prepared as described in Example 1 except that the drying process for the catalyst formulation was adjusted to dry at 60° C. for 48 hours followed by treating at 210° C. for 15 hours. The reaction conditions were the same as those of Example 1. After 50 hours of reaction at 360° C., the propylene conversion ratio was 97.8%, acrolein yield was 80.4%, acrylic acid yield was 7.2%, and COx yield was 3.6%.

Example 5

First, 4500 ml water was added into a beaker and heated to 75° C., 1412.6 g ammonium molybdate and 7.8 g potassium nitrate were added thereto, the mixture was stirred to dissolve and form a solution (A), which was maintained at 75° C. Next, 1300 ml water was added into another beaker and heated to 70° C., 1058.4 g cobalt nitrate, 511.9 g nickel nitrate and 546.6 g ferric nitrate were added thereto sequentially, the mixture was stirred to dissolve, then 50 ml nitric acid and 490.2 g bismuth nitrate were added thereto, the mixture was stirred to dissolve and form a solution (B), which was maintained at 50~70° C. Solution (B) was added dropwise into solution (A) with intense stirring at 70° C. within 10 minutes, in the meantime an aqueous solution of urea (10 wt %) was added to keep pH of the slurry at 1.6, and the mixture was stirred after the addition was finished until the slurry was homogenously mixed. The slurry was spray dried at 180° C. followed by treated at 210° C. for 15 hours. The resultant sample was mixed with silicon at 7:3 ratio (w/w), 3 wt % graphite and 2 wt % (based on silica) silica gel were added, the resultant mixture was compression molded into a 3 mm long hollow cylinder with an external diameter of 5 mm and internal diameter of 2 mm, and fired at 515° C. to produce the finished catalyst.

50 g of the catalyst was filled into a stationary bed tubular reactor, preheated gas mixture of propylene, air, steam and nitrogen with a molar ratio of propylene:oxygen:water:nitrogen rather than that from the air being 1:1.8:2.5:2.5 was passed through the reactor at an overall space velocity of 1850 $h^{-1}$, the oxidation reaction was conducted at 320° C. under normal pressure. After 24 hours of reaction at 342° C., the propylene conversion ratio was 99.0%, acrolein yield was 83.5%, acrylic acid yield was 9.4%, and COx yield was 3.3%.

Example 6

The catalyst was prepared as described in Example 5 except that 2 wt % of molybdenum oxide was added during the molding process serving as an aids. The reaction conditions were the same as those of Example 5. After 24 hours of reaction at 343° C., the propylene conversion ratio was 98.6%, acrolein yield was 84.2%, acrylic acid yield was 9.7%, and COx yield was 2.8%.

Example 7

First, 4500 ml water was added into a beaker and heated to 75° C., 1512.6 g ammonium molybdate and 6.1 g potassium nitrate were added thereto, the mixture was stirred to dissolve and form a solution (A), which was maintained at 75° C. Next, 1300 ml water was added into another beaker and heated to 70° C., 1058.4 g cobalt nitrate, 511.9 g nickel nitrate and 546.6 g ferric nitrate were added thereto sequentially, the mixture was stirred to dissolve, then 50 ml nitric acid and 490.2 g bismuth nitrate were added, the mixture was stirred to dissolve and form a solution (B), which was maintain at 50~70° C. Solution (B) was added dropwise into solution (A) with intense stirring at 70° C. within 10 minutes, in the meantime aqua ammonia was added to keep pH of the slurry at 2.0, and the mixture was stirred after the addition was finished while 1000 g silicon was added until homogenized. The slurry was dried at 155° C. within 1 hour, followed by treated at 210° C. for 15 hours. 1.5 wt % graphite and 1.5 wt % (based on silica) silica gel were added into the obtained sample, the resultant mixture was compression molded into a 3 mm long hollow cylinder with an external diameter of 5 mm and an internal diameter of 2 mm, and fired at 512° C. to produce the finished catalyst.

50 g of the catalyst was filled into a stationary bed tubular reactor, preheated gas mixture of propylene, air, steam and nitrogen with a molar ratio of propylene:oxygen:water:nitrogen other than that from the air being 1:1.7:1.6:1.6 was passed through the reactor at an overall space velocity of 1450 $h^{-1}$, the oxidation reaction was conducted at 330° C. under normal pressure. After 24 hours of reaction at 348° C., the propylene conversion ratio was 99.0%, acrolein yield was 83.0%, acrylic acid yield was 9.5%, and COx yield was 2.9%.

Example 8

First, 4500 ml water was added into a beaker and heated to 75° C., 1512.6 g ammonium molybdate and 6.1 g potassium nitrate were added thereto, the mixture was stirred to dissolve and form a solution (A), which was maintained at 75° C. Next, 1300 ml water was added into another beaker and heated to 70° C., 1058.4 g cobalt nitrate, 511.9 g nickel nitrate and 546.6 g ferric nitrate were added thereto sequentially, the mixture was stirred to dissolve, then 50 ml nitric acid and 490.2 g bismuth nitrate were added thereto, and the mixture was stirred to dissolve and form a solution (B), which was maintained at 50~70° C. Solution (B) was added dropwise into solution (A) with intense stirring at 70° C. within 10 minutes, and the mixture was stirred after the addition was finished while 1000 g silicon was added until homogenized. The slurry was dried at 155° C. within 1 hour, followed by treated at 210° C. for 15 hours. 1.5 wt % graphite and 1.5 wt % (based on silica) silica gel were added into the obtained sample, the resultant mixture was compression molded into a 3 mm long hollow cylinder with an external diameter of 5 mm and an internal diameter of 2 mm, and fired at 512° C. to produce the finished catalyst.

50 g of the catalyst was filled into a stationary bed tubular reactor, preheated gas mixture of propylene, air, steam and nitrogen with a molar ratio of propylene:oxygen:water:nitrogen other than that from the air being 1:1.7:1.6:1.6 was passed through the reactor at an overall space velocity of 1450 $h^{-1}$, the oxidation reaction was conducted at 315° C. under normal pressure. After 24 hours of reaction at 335° C., the propylene conversion ratio was 98.8%, acrolein yield was 78.3%, acrylic acid yield was 7.6%, and COx yield was 6.5%.

Example 9

The catalyst was prepared as described in Example 8 except that aqua ammonia was added during the preparation to keep the pH of the slurry at 6.0. The reaction conditions were the same as those of Example 8. After 24 hours of reaction at 340° C., the propylene conversion ratio was 98.25%, acrolein yield was 79.2%, acrylic acid yield was 7.7%, and COx yield was 5.5%.

Example 10

First, 5000 ml water was added into a beaker and heated to 70° C., 1412.6 g ammonium molybdate, 7.8 g potassium nitrate and 520.0 g ammonium tungstate were added thereto, the mixture was stirred to dissolve and form a solution (A), which was maintain at 75° C. Next, 1300 ml water was added into another beaker and heated to 70° C., 1058.4 g cobalt nitrate and 546.6 g ferric nitrate were added thereto sequentially, the mixture was stirred to dissolve, then 35 ml nitric acid and 490.2 g bismuth nitrate were added thereto, the resultant mixture was stirred to dissolve and form a solution (B), which was maintained at 50~70° C. Solution (B) was added dropwise into solution (A) with intense stirring at 70° C. within 10 minutes, in the meantime aqua ammonia was added to keep pH of the slurry at 2.5, and the mixture was stirred after the addition was finished until the slurry was homogenized. The slurry was dried at 150° C. within 2 hours followed by treated at 240° C. for 10 hours. The resultant product was mixed with silicon at 7.3:2.7 ratio (w/w), based on weight of the resultant mixture, 3 wt % graphite and 2 wt % (based on silica) silica gel were added, the mixture was band extruded into a 4 mm long hollow cylinder with an external diameter of 4.5 mm and an internal diameter of 2 mm, then fire at 520° C. to produce the finished catalyst.

50 g of the catalyst was filled into a stationary bed tubular reactor, preheated gas mixture of propylene, air, steam and nitrogen with a molar ratio of propylene:oxygen:water:nitrogen other than that from the air being 1:1.6:1.5:1.5 was passed through the reactor at an overall space velocity of 1400 h$^{-1}$, the oxidation reaction was conducted at 330° C. under normal pressure. After 24 hours of reaction at 350° C., the propylene conversion ratio was 97.8%, acrolein yield was 83.0%, acrylic acid yield was 8.4%, and COx yield was 3.3%.

Example 11

The catalyst was prepared as described in Example 10 except that the ammonium tungstate in solution (A) was omitted and 503.5 g zinc nitrate was added into solution (B). The reaction conditions were the same as those of Example 10. After 24 hours of reaction at 352° C., the propylene conversion ratio was 97.9%, acrolein yield was 83.2%, acrylic acid yield was 8.8%, and COx yield was 3.2%.

Example 12

The catalyst was prepared as described in Example 11 except that the zinc nitrate in solution (B) was omitted and 650.3 g chromium nitrate was added instead. The reaction conditions were the same as those of Example 11. After 24 hours of reaction at 355° C., the propylene conversion ratio was 98.2%, acrolein yield was 82.8%, acrylic acid yield was 8.5%, and COx yield was 3.1%.

Example 13

The catalyst was prepared as described in Example 10.

60 g of the catalyst was fill into a stationary bed tubular reactor, preheated gas mixture of isobutylene, air and steam with a molar ratio of isobutylene:oxygen:water:nitrogen being 1:2:1.5:12 was passed through the reactor at an overall space velocity of 1400 h$^{-1}$, the oxidation reaction was conducted at 340° C. under normal pressure. After 100 hours of reaction at 360° C., the isobutylene conversion ratio was 98.9%, methacrolein yield was 89.9%, and methacrylic acid yield was 4.5%.

What is claimed is:

1. A method of preparing a catalyst used for producing unsaturated aldehyde by the oxidation of lower olefin at a high space velocity, said catalyst is a Mo—Bi—Fe—Co based composite metal oxide represented by a formula of

$$Mo_aBi_bFe_cCo_dX_eY_fZ_gO_h,$$

wherein
Mo is a molybdenum atom;
Bi is a bismuth atom;
Fe is an iron atom;
Co is a cobalt atom;
X is at least one atom selected from tungsten (W), antimony (Sb), arsenic (As), phosphorus (P), nickel (Ni), tin (Sn), and plumbum (Pb);
Y is at least one atom selected from zinc (Zn), chromium (Cr), manganese (Mn), ruthenium (Ru), silver (Ag), palladium (Pd) and ruthenium (Ru);
Z is at least one atom selected from sodium (Na), potassium (K), lithium (Li), rubidium (Rb), cesium (Cs), calcium (Ca), magnesium (Mg), strontium (Sr), and barium (Ba); and
each of a, b, c, d, e, f and g represents the atomic ratio of each atom, with the proviso that when a=12, b=0.1~7, c=0.5~8, d+e=0.5~20, f=0~1, g=0~2, and h is a number determined by the oxidation state of each atom;
said catalyst is prepared by co-precipitation, i.e. the precursor compounds for the catalyst are co-precipitated to obtain a slurry at pH 1.5~3.0, the slurry is rapidly dried, then silicon powder as a diluting thermal conductor is added and the mixture is molded and fired to produce the finished catalyst; alternatively, a diluting thermal conductor can be added into the slurry prior to the rapid drying, then the dried mixture is molded and fired to produce the finished catalyst.

2. The method according to claim 1, wherein the molybdenum atom in the composite metal oxide of the catalyst is derived from phosphomolybdic acid, molybdate or molybdenum oxide; the tungsten atom is derived from tungstate or tungsten trioxide; the alkali metal or alkaline earth metal atom is derived from their corresponding hydroxide or nitrate; and the other atoms are derived from their corresponding acetate, nitrate, chloride or oxide.

3. The method according to claim 1, wherein a basic solution is employed to adjust the pH and maintain the pH of the slurry in the range of 1.5~3.0 during the co-precipitation of the precursor compounds for the composite metal oxide of the catalyst, and wherein said basic solution is selected from aqua ammonia or aqueous solution of urea.

4. The method according to claim 1, wherein the slurry of the precursor compounds for the composite metal oxide of the catalyst or the slurry containing the diluting thermal conductor is dried in an apparatus capable of drying the slurry into a dried powder having water content of between 8 to 10 wt % within 1.8~2.2 hours.

5. The method according to 1, wherein the obtained dried powder of the precursor compounds for the composite metal oxide of the catalyst is homogenously mixed with the diluting thermal conductor, a binder and a molding aid, or the obtained dried powder of the precursor compounds for the composite metal oxide of the catalyst containing the diluting thermal conductor is homogenously mixed with a binder and a molding aid, the resultant mixture is coated onto an inert carrier or directly molded by compression or band extrusion to form solid or hollow particles in the shape of sphere, cylinder, trefoil, quatrefoil, or gear, and wherein the amount of the diluting thermal conductor is in the range of 0~50 wt %, the amount of the binder is in the range of 0.01~10 wt %, and the amount of the molding aid is in the range of 0.01~10 wt %, all relative to the overall weight of the powder.

6. The method according to claim 1, wherein the molded catalyst is fired at 420~550° C. in an atmosphere comprising 1~21 wt % of oxygen molecules for 1~20 hours, wherein the oxygen molecules in the atmosphere is from air or purified oxygen, and the balance amount of the atmosphere is nitrogen, steam, helium, argon, or any combination thereof, and wherein the space velocity of the firing atmosphere relative to the catalyst is in the range of 10~1500 $h^{-1}$.

7. The method according to claim 1, wherein said lower olefin is propylene or iso-butylene and said unsaturated aldehyde is acrolein or methacrolein.

8. A catalyst composition, comprising
60-90% by weight of a catalyst; and
10-40% by weight of a diluting thermal conductor, wherein said catalyst is a Mo—Bi—Fe—Co based composite metal oxide represented by a formula of:

$$Mo_aBi_bFe_cCo_dX_eY_fZ_gO_h,$$

wherein
Mo is a molybdenum atom;
Bi is a bismuth atom;
Fe is an iron atom;
Co is a cobalt atom;
X is at least one atom selected from tungsten (W), antimony (Sb), arsenic (As), phosphorus (P), nickel (Ni), tin (Sn), and plumbum (Pb);
Y is at least one atom selected from zinc (Zn), chromium (Cr), manganese (Mn), ruthenium (Ru), silver (Ag), palladium (Pd) and ruthenium (Ru); and
Z is at least one atom selected from sodium (Na), potassium (K), lithium (Li), rubidium (Rb), cesium (Cs), calcium (Ca), magnesium (Mg), strontium (Sr), and barium (Ba); and
each of a, b, c, d, e, f and g represents the atomic ratio of each atom, with the proviso that when a=12, b=0.1~7, c=0.5~8, d+e=0.5~20, f=0~1, g=0~2, and h is a number determined by the oxidation state of each atom;

characterized in that said catalyst composition is obtained by a process comprises the steps of:

co-precipitating the precursor compounds for the catalyst to form a slurry at pH 1.5~3.0;

rapidly drying the slurry;

adding silicon powder as a diluting thermal conductor and molding the mixture; and firing to produce the finished catalyst;

alternatively, co-precipitating the precursor compounds for the catalyst to form a slurry at pH 1.5~3.0;

adding a diluting thermal conductor and rapidly drying the slurry;

molding the mixture; and firing to produce the finished catalyst.

9. The catalyst composition of claim 8, comprising 70-80% by weight of a catalyst and 20-30% by weight of a diluting thermal conductor.

* * * * *